United States Patent
Charlez et al.

(10) Patent No.: US 9,861,715 B2
(45) Date of Patent: Jan. 9, 2018

(54) BODY FLUID DRAINAGE DEVICE AND METHOD

(71) Applicant: Observe Medical ApS, Kongens Lyngby (DK)

(72) Inventors: Mikael Charlez, Molndal (SE); Mikael Lofgren, Molndal (SE)

(73) Assignee: OBSERVE MEDICAL APS, Kongens, Lyngby (DK)

( * ) Notice: Subject to any disclaimer, the term of this patent is extended or adjusted under 35 U.S.C. 154(b) by 0 days.

(21) Appl. No.: 15/509,540

(22) PCT Filed: Sep. 15, 2015

(86) PCT No.: PCT/EP2015/071058
§ 371 (c)(1),
(2) Date: Mar. 8, 2017

(87) PCT Pub. No.: WO2016/041941
PCT Pub. Date: Mar. 24, 2016

(65) Prior Publication Data
US 2017/0258952 A1 Sep. 14, 2017

(30) Foreign Application Priority Data
Sep. 15, 2014 (SE) ...................................... 1451078

(51) Int. Cl.
*B05D 5/00* (2006.01)
*C02F 1/32* (2006.01)
(Continued)

(52) U.S. Cl.
CPC .............. *A61L 2/081* (2013.01); *A61B 5/208* (2013.01); *A61B 5/6852* (2013.01); *A61L 2/082* (2013.01);
(Continued)

(58) Field of Classification Search
USPC ...... 250/428, 432 R, 436, 437, 458.1, 459.1, 250/461.1; 210/428, 432 R, 436, 437,
(Continued)

(56) References Cited

U.S. PATENT DOCUMENTS 3,919,455 A * 11/1975 Sigdell .................. A61B 5/208
73/226
3,962,519 A * 6/1976 Rusch ..................... A61L 29/06
128/DIG. 21
(Continued)

FOREIGN PATENT DOCUMENTS

EP  0 173 450 A2  3/1986
EP  0 496 633 A1  7/1992
(Continued)

OTHER PUBLICATIONS

International Search Report for corresponding International Application No. PCT/EP2015/071058 dated Jan. 5, 2016.
(Continued)

*Primary Examiner* — Bernard Souw
(74) *Attorney, Agent, or Firm* — RMCK Law Group PLC

(57) ABSTRACT

Method for sterilizing a body fluid drainage system for handling a body fluid ex vivo. The body fluid drainage system comprises a chamber. The method comprises the steps providing a container containing a surface protective fluid to be released into the chamber of the body fluid drainage system, subjecting the container to radiation sterilization, inserting the container into the chamber of the body fluid drainage system, and subjecting the chamber containing the container to gas sterilization. A body fluid drainage system for handling a body fluid ex vivo. The body fluid drainage system comprises a chamber. The body fluid drainage system further comprises a container containing a surface protective fluid. The container is arranged to release the surface protective fluid into the chamber. The surface (Continued)

protective fluid is sterilized by radiation sterilization. An outer surface of the container and at least the chamber of the body fluid drainage system is sterilized by gas sterilization.

13 Claims, 1 Drawing Sheet

(51) Int. Cl.

| | | |
|---|---|---|
| C02F 1/30 | (2006.01) | |
| A61L 2/08 | (2006.01) | |
| A61L 2/20 | (2006.01) | |
| A61M 25/00 | (2006.01) | |
| A61B 5/20 | (2006.01) | |
| A61B 5/00 | (2006.01) | |
| A61B 90/70 | (2016.01) | |

(52) U.S. Cl.
CPC ............... *A61L 2/087* (2013.01); *A61L 2/202* (2013.01); *A61L 2/204* (2013.01); *A61L 2/208* (2013.01); *A61M 25/0017* (2013.01); *A61B 2090/701* (2016.02); *A61L 2202/23* (2013.01); *A61M 2025/0019* (2013.01)

(58) Field of Classification Search
USPC ..... 210/458.1, 459.1, 461.1; 422/186.3, 186, 422/24, 40, 41, 44
See application file for complete search history.

(56) References Cited

U.S. PATENT DOCUMENTS

| | | | |
|---|---|---|---|
| 4,186,745 A | 2/1980 | Lewis et al. | |
| 5,635,133 A * | 6/1997 | Glazman | A61L 2/10 250/432 R |
| 6,017,334 A | 1/2000 | Rawls | |
| 6,228,635 B1 * | 5/2001 | Armstrong | C12M 23/42 435/283.1 |
| 6,328,937 B1 * | 12/2001 | Glazman | A61L 9/20 422/121 |
| 6,501,893 B1 * | 12/2002 | Iimura | G01N 21/7703 385/12 |
| 7,147,625 B2 | 12/2006 | Sarangapani et al. | |
| 8,747,764 B1 * | 6/2014 | Burchman | A61L 2/0047 210/153 |
| 2005/0192560 A1 * | 9/2005 | Walls | A61M 25/0015 604/544 |
| 2008/0156092 A1 * | 7/2008 | Boiarski | A61B 10/007 73/304 R |
| 2008/0279733 A1 * | 11/2008 | Glazman | A61L 9/20 422/186.3 |
| 2011/0146680 A1 * | 6/2011 | Conway | A61L 29/06 128/204.18 |
| 2011/0208026 A1 * | 8/2011 | Goodall | A61L 2/0011 600/345 |
| 2011/0301553 A1 | 12/2011 | Goral et al. | |
| 2016/0038070 A1 * | 2/2016 | Charlez | A61B 5/208 73/304 C |

FOREIGN PATENT DOCUMENTS

| | | |
|---|---|---|
| EP | 1 308 146 A1 | 5/2003 |
| GB | 1093751 A | 12/1967 |
| GB | 1323083 A | 7/1973 |
| GB | 2 417 231 A | 2/2006 |
| SE | 1 350 318 A1 | 9/2014 |
| WO | 1989005671 A1 | 6/1989 |
| WO | 2000/043049 A1 | 7/2000 |
| WO | 2000043049 A1 | 7/2000 |
| WO | 2001/023007 A1 | 4/2001 |
| WO | 2003097237 A2 | 11/2003 |
| WO | 2008107385 A1 | 9/2008 |
| WO | 2008115439 A1 | 9/2008 |
| WO | 2010/149708 A1 | 12/2010 |
| WO | 2014043650 A2 | 3/2014 |
| WO | 2014/140328 A1 | 9/2014 |

OTHER PUBLICATIONS

Written Opinion of the International Searching Authority for corresponding International Application No. PCT/EP2015/071058 dated Jan. 5, 2016.
International Preliminary Report on Patentability for corresponding International Application No. PCT/EP2015/071058 dated Jan. 5, 2016.
International-Type Search Report for corresponding National Application No. 1451078-8 dated Jul. 6, 2015.

* cited by examiner

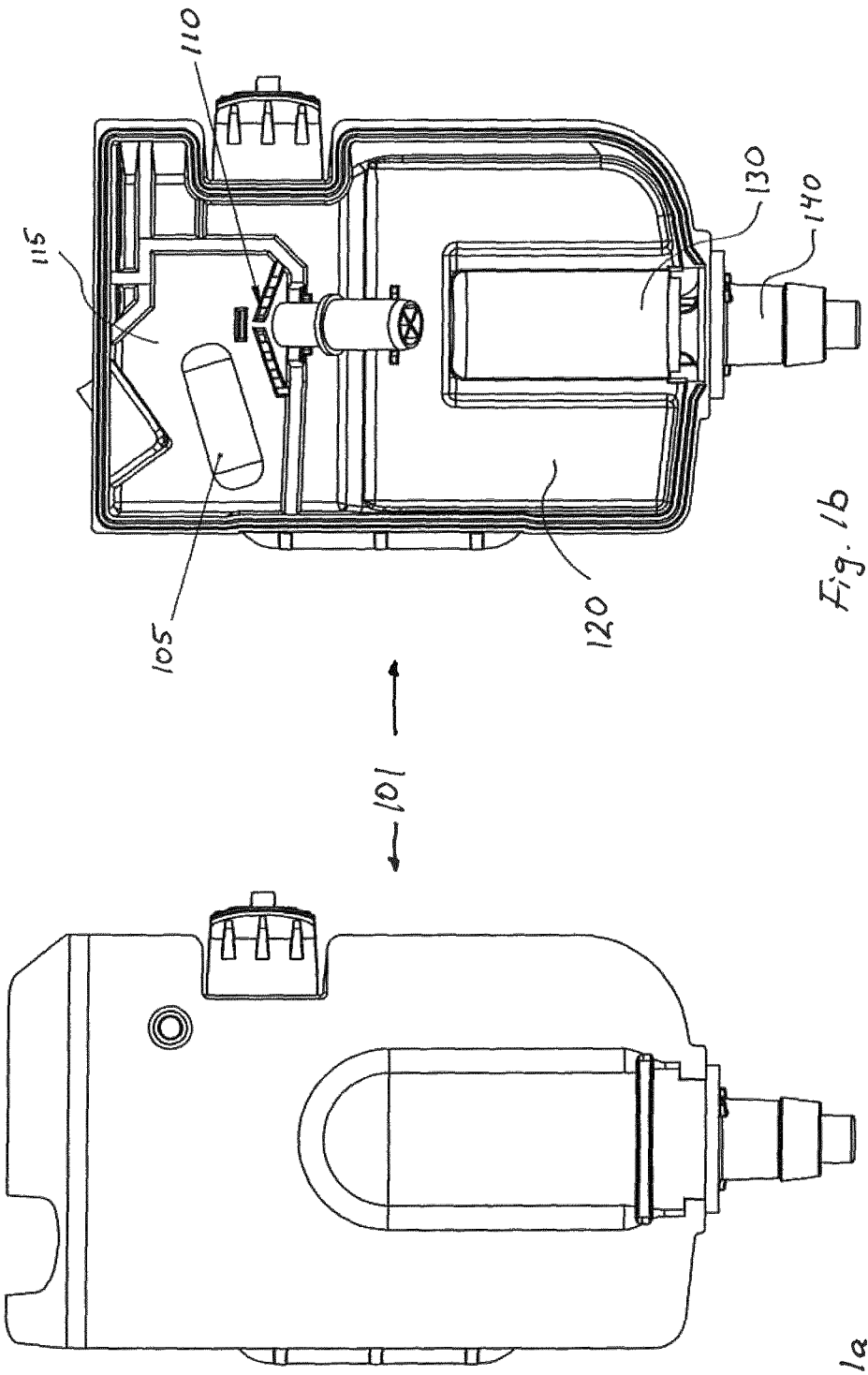

BODY FLUID DRAINAGE DEVICE AND METHOD

This application is a national phase of International Application No. PCT/EP2015/071058 filed Sep. 15, 2015 and published in the English language, which claims priority to Application No. SE 1451078-8 filed Sep. 15, 2014.

TECHNICAL FIELD

The present invention relates to a device and a method for handling of body fluid of a patient wearing a drainage. More specifically it relates to a method for sterilising a body fluid drainage system and a sterilised body fluid drainage system.

BACKGROUND ART

Examples of electronic body fluid measurement systems known in the art are electronic urine measurement systems such as:

WO 2010/149708 A1 discloses a urine measurement device for measuring urine production of a patient having a urine catheter. The device uses capacitive measurements from electrodes arranged close to a self emptying measurement chamber to calculate the urine level in the measurement chamber.

U.S. Pat. No. 3,919,455 describes a device comprising a siphon chamber for the urine with a self emptying function, and wherein the urine volume is measured with the aid of an optic and/or electric sensor. When the urine level in the siphon chamber increases, the capacitance between two electrodes in the walls of the siphon chamber changes. In this way a signal is created that corresponds to the amount of urine in the siphon chamber. See e.g. FIG. 4 and column 4 lines 34 to 52.

US20110146680A1 discloses a method for manufacturing a silicone catheter wherein the catheter is immersed in oil before it is immersed in a liquid comprising the antimicrobial substance chlorhexidine gluconate in order to make the chlorhexidine gluconate better adhere to the catheter.

Different methods for sterilising medical products and devices have been suggested such as:

WO 00/43049 A1 discloses a method of packaging a medicinal product by depositing the medicinal product in a container and exposing the container to gamma irradiation.

WO 01/23007 A1 discloses a device for draining urine. The device includes a collection bag including an elongated neck-like portion and a collection portion. A catheter is packed inside the collection bag in the region corresponding to the elongated portion and can be extracted therefrom when the device is to be used. The elongated portion has an opening at its distal end for allowing extraction of the catheter. The device includes a segment of liquid-impermeable material removably fastened to the elongated portion at its distal end. The liquid-impermeable material can be permeated by gases, which are commonly used for sterilisation, for instance ethylene oxide.

SUMMARY OF THE INVENTION

Urine meter systems in general are depending on a connection to a urine drainage, i.e. a catheter, in order to get access to the urine-bladder and drain urine from the bladder through a tubing system. The urine is led through a measuring unit and then collected in a collection bag.

Urinary Tract Infection (UTI) is the most common nosocomial infection within the healthcare system today. The UTI extends length of stay, increase costs and contributes to an additional risk to the patients' health status. It's usually related to the installation of said urine catheter. It's revealed through clinical research that the risk of UTI increases by 10% each day the catheter stays in the urinary tract. Bacteria has either their entrance from the outside of the body (64%) or from the very inside (36%).

The inventors have realised, with the aid of literature studies that in in-vitro system bacterial colonisation generates a bio film that becomes mineralised (encrustation). In sterile urine, the development of encrustation has been shown to be dependent on urinary properties such as pH and ionic strength as well as on the biomaterial hydrophobic properties. Urine is generally free from bacteria and thus it is the chemistry of the urine in a measuring and/or collecting environment that dominates the variables. In infected urine, enzyme urease produced by adhered bacteria hydrolyses the urea to produce ammonia. This elevates the urine pH, a condition that favours the precipitation of magnesium and calcium in the form of struvite and hydroxyapatite (HA). These minerals are two major component of encrustation. Similar problems can be found in drainage systems for other body fluids.

Said bio-film and related risk of nosocomial UTIs are not visible to the human naked eye, at least not in the early stages of formation.

Sensor arrangement, signal processing, and signal interpretation methods of signals coming from a capacitive sensor system of a body fluid measurement system for measuring body fluid production of a patient wearing a body fluid drainage, e.g. a urine measurement system for measuring the urine production of a patient having a urine catheter, may all suffer from harder measuring conditions that are likely to arise over time during prolonged use of such a measuring system.

The inventors have presented the idea that surface degeneration may impair function of a capacitive measuring system and may cause a dysfunction of the siphon portion of the self-emptying chamber. They have conducted experiments around how the presence of a surface protective fluid, such as a purpose selected oil, in the measurement chamber of the siphon system prolongs operational life of the same. They have also suggested that priming of luminal surfaces of the system may be achieved by self-priming with the aid of the body fluid flowing through the system. Furthermore, they have suggested a way to sterilise the system.

The above mentioned inconveniences may be improved by applying a surface protective fluid, such as a low viscosity oil, to the inner surfaces of a body fluid handling system, with the purpose of arriving at a body fluid handling system with sustained functional reliability and sustained measurement accuracy, in particular during prolonged use. The effect may be due to the oil influencing factors affecting bacterial growth and bio-film formation. The effect may also come from other mechanisms or from a synergetic effect not yet fully understood.

The body fluid handling system may be of a measurement type having a capacitive sensor system working together with a self emptying measurement chamber. The body fluid handling system may be provided with a container, such as capsule of a material that will disintegrate when coming into contact with body fluid, e.g. a water soluble material. The capsule may initially be filled with a purpose selected oil and when the capsule disintegrates the oil is transported with the aid of the body fluid flow to become applied to those surfaces of the body fluid handling system that becomes exposed to body fluid.

Application of a surface protective fluid, such as a low viscosity oil, is particularly useful in systems that use electronic methods for measuring the amount of body fluid passing through the system, for example capacitive measurement methods. It will also provide an advantage in systems using self emptying chamber(s) to handle body fluid measurements. Tests have shown that the self emptying function of such chambers will continue to function reliably for several days, while within a system without the solution of the present invention, functionality may be compromised as soon as after 24 hours.

A body fluid measurement system may comprise a chamber, such as a well defined measurement chamber for temporarily collecting an amount of body fluid to measure. The chamber may be of a self emptying siphoning type, that is, the chamber, when it becomes full, empties itself by means of siphoning technique.

In order to reduce the risk of infecting the patient it is important that the body fluid handling system is sterile. It is in particular important that the surfaces of the body fluid handling system that comes in contact with the body fluid, such as the inner surfaces of the chamber of the body fluid handling system, are sterile. In order to not contaminate these surfaces of the body fluid handling system it is important that the surface protective fluid, such as the oil, also is sterile.

Thus, according to a first aspect of the present invention there is provided a method for sterilising a body fluid drainage system for handling a body fluid ex vivo. The body fluid drainage system comprises a chamber. The method comprises the following steps:

providing a container containing a surface protective fluid to be released into the chamber of the body fluid drainage system,
subjecting the container to radiation sterilisation,
inserting the container into the chamber of the body fluid drainage system,
subjecting the chamber containing the container to gas sterilisation.

In some aspects of the above method, the method further comprises the step enclosing the container in a sealed enclosure, which enclosing step is performed before subjecting the container to radiation sterilisation.

According to a second aspect of the present invention there is provided a method for sterilising a body fluid drainage system for handling a body fluid ex vivo. The body fluid drainage system comprises a chamber. The method comprises the following steps:

providing a container containing a surface protective fluid to be released into the chamber of the body fluid drainage system, which container has been subjected to radiation sterilisation,
inserting the container into the chamber of the body fluid drainage system, and
subjecting the chamber containing the container to gas sterilisation.

In some aspects of the above latter method, the provided container has been enclosed in a sealed enclosure before it was subjected to radiation sterilisation.

In some aspect of any of the above methods, the container is a capsule comprising a capsule wall made of a water-soluble material.

In some aspect of any of the above methods, the surface protective fluid is an oil mixture comprising 90-100% of an oil selected from the group consisting of silicone fluids and mineral oils or a mixture thereof, and having a viscosity of at most 600 cSt.

The container is sterilised using radiation sterilisation so that both the surface and the content of the container is sterilised. The chamber is sterilised using gas sterilisation so that the surfaces, in particular the inner surfaces, of the chamber as well as the outer surface of the container are sterilised.

According to a third aspect of the present invention there is provided a body fluid drainage system for handling a body fluid ex vivo. The body fluid drainage system comprises a chamber and the body fluid drainage system further comprises a container containing a surface protective fluid, wherein the container is arranged to release the surface protective fluid into the chamber. The surface protective fluid is sterilised by radiation sterilisation. An outer surface of the container and at least the chamber of the body fluid drainage system is sterilised by gas sterilisation.

In some aspects of the body fluid drainage system, the container is disposed in the chamber.

In some aspects of the body fluid drainage system, the container is a capsule comprising a capsule wall made of a water-soluble material.

In some aspects of the body fluid drainage system, the surface protective fluid is an oil mixture comprising 90-100% of an oil selected from the group consisting of silicone fluids and mineral oils or a mixture thereof, and having a viscosity of at most 600 cSt.

According to a fourth aspect of the present invention there is provided a body fluid drainage system for handling a body fluid ex vivo. The body fluid drainage system comprises a chamber and the body fluid drainage system further comprises a container containing a surface protective fluid, wherein the container is arranged to release the surface protective fluid into the chamber. The body fluid drainage system is sterilised by any of the above methods.

In some aspects, the container is a body fluid drainage system container for releasing a surface protective fluid into a lumen of a body fluid drainage system handling a body fluid ex vivo.

In some aspects, the container is disposed in the chamber.

In some aspects, the container contains a surface protective fluid and the container is adapted to release the surface protective fluid when the body fluid drainage system is put in operation.

In some aspects, the container is a capsule comprising a capsule wall made of a water-soluble material.

In some aspects, the capsule wall defines a space filled with the surface protective fluid.

In some aspects, the water-soluble material is selected from the group consisting of hydroxypropyl methylcellulose and polyvinyl alcohol (PVOH) or a mixture thereof.

In some aspects, the surface protective fluid is an oil mixture comprising 90-100% of an oil selected from the group consisting of silicone fluids and mineral oils or a mixture thereof, and having a viscosity of at most 600 cSt.

In some aspects, the viscosity of the oil is in the interval of 200 to 600 cSt, such as in the interval of 300 to 400 cSt, such as in the interval of 345 to 355 cSt, such as about 350.

In some aspects, the oil mixture is selected from the group of silicone fluids.

In some aspects, the oil mixture is selected from the group of linear polydimethylsiloxanes.

In some aspects, the oil mixture is void of antimicrobial agent.

In some aspects, the body fluid drainage system further comprises an electronic measurement system comprising electrodes arranged outside said chamber to measure changing capacitance values as body fluid level inside the chamber increases.

In some aspects, the chamber comprises a self-emptying siphoning arrangement arranged to empty itself by means of siphoning technique.

In some aspects, the container is arranged upstream of the chamber or in an upstream portion of the chamber and is prevented from entering the chamber by a grate.

In some aspects, the grate is made of a metal or polymer material.

In some aspects, the material of the chamber is selected from a group consisting of polymer materials.

In some aspects, the material of the chamber is selected from a group consisting of glass materials.

In some aspects, the material of the chamber is selected from a group of materials having lipophilic properties.

In some aspects, the body fluid is urine.

The surface protective fluid is sterile. The surface protective fluid is sterilised by radiation sterilisation.

At least the chamber of the body fluid drainage system is sterile. Further parts or portions of the body fluid drainage system may be sterile. Also the container is sterile. At least the chamber of the body fluid drainage system is sterilised by gas sterilisation. Further parts or portions of the body fluid drainage system may be sterilised by gas sterilisation. Also the container is sterilised by gas sterilisation.

BRIEF DESCRIPTION OF THE DRAWINGS

The invention will now be further explained with the aid of one or more embodiments of the invention in conjunction with the accompanying drawings of which:

FIG. 1a is a front view of a measurement chamber of a body fluid handling system.

FIG. 1b is view of the measurement chamber of FIG. 1a wherein a front wall is removed exposing the inner structure including capsule/oil pill arrangement and grate arrangement.

DETAILED DESCRIPTION

Definitions

In the context of the present invention the following terms and phrases will be used having the following meanings:

A "body fluid handling system" denotes a system for handling of body fluid emanating from a human patient involved in a care situation, including but not limited to, a nursing situation and a treatment situation.

A "body fluid measurement system" denotes a system designed to measure the amount of body fluid emanating from a human patient involved in a care situation, including but not limited to, a nursing situation and a treatment situation.

The term "silicone fluid" is intended to include silicone oils such as silicone esters or other liquid silicone compounds with the general formula:

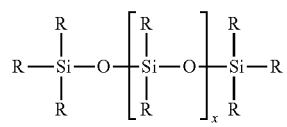

where each R can be an aliphatic group such as an alkyl group, for example a methyl, ethyl or propyl radical or alkoxy group or a phenyl group, or combinations thereof; and where x has a value of from about 0 to about 10,000, preferably from about 1 to about 200, and most preferably from about 10 to about 125.

The term "body fluid" is intended to include all kinds of bodily fluids, i.e. biofluids originating from inside of a body of a living person. Examples of body fluids are: urine, blood, pus, lymph, abdominal fluid, spinal fluid, cerebral/spinal fluid and ascites.

The Problem

Body fluids such as urine may be very aggressive on manmade surfaces, in particular on surfaces inside a body fluid drainage system, such as a body fluid measurement system. The body fluid drainage system according to the invention may be a closed system that comprises a tubing system connected to a patient's drainage, e.g. a catheter, a chamber, such as a measurement chamber, intermediate chamber or analyse chamber, and a collection bag. The body fluid drainage system is located outside the body of a patient, i.e. ex vivo. The tubing system leads the body fluid from the patient to the chamber, such as a measurement chamber where a capacitive, contact-less sensor system senses the signals through the wall of the measurement chamber, and thereof calculates the volume. The chamber wall is preferably of a rigid polymeric material, easily obtained in medical equipment grades. The body fluid is preferably collected in a collection bag after it has been measured or analysed. Such a collection bag is preferably made of a flexible polymeric material, and has a volume considerably larger than the volume of the chamber.

The chamber is preferably devised to self-empty at a certain volume around 15-20 ml. The challenge in said self-emptying chamber is to handle the effects of degenerative process compromising the electric and physical properties of the delicate surfaces of the chamber caused by the body fluid over time.

Thus, and as also mentioned above, the inventor has realised, and also experienced, that within an unforeseeable amount of time there is a decrease of signal through the chamber wall that seems to be caused by a bio film formation on the surface(s) corresponding to where the sensors are arranged. There seems to be a considerable risk of a degeneration of the delicate surfaces within the region of the self-emptying system which may lead to a dysfunction of the self-emptying mechanism.

One solution to the problem would be to replace the chamber when signs of dysfunction are noticeable. However, it would be an advantage if this could be avoided, since it requires more resources.

The Solution

Now turning to FIGS. 1a and 1b, the present invention teaches to apply a substance to the surfaces of the body fluid drainage system to improve sustained functionality and accuracy, such as measurement functionality and accuracy.

If a body fluid drainage system provided with a chamber 101 comprising a siphoning self-emptying arrangement begins to execute premature emptying sequences, it is likely that surface(s) of the chamber 101 critical to initiation of the self-emptying sequence, has become compromised. The solution involves arranging an oil releasing device 105 early in the flow path of the body fluid measurement system, and to let said oil releasing device 105 release oil into the system for adhering to the luminal surfaces of the system. Subsequent to release, the body fluid aids in dispersing the oil, the body fluid being an aqueous, oil repellant fluid. The oil gets on top of the body fluid, and during a filling phase of the chamber, takes with it the oil, which oil adheres to the luminal surfaces in need thereof.

The oil is an example of a surface protective fluid. The surface protective fluid is a fluid that adheres to the inner surface of the chamber and prevents other fluids from coming into contact with the surface. When the surface protective fluid is an oil, aqueous fluids and oil repellent fluids are repelled from the surface.

It is realised by the skilled reader that this measure of providing an oil releasing device would improve not only a body fluid measurement system, but any body fluid drainage or handling system liable or susceptible to degradation over time.

The present invention relates to a method for improving sustained functionality and measurement accuracy in a body fluid drainage system having inner surfaces coming into contact with body fluid, the method comprising the following step(s):

applying an oil mixture to the inner surfaces of the body fluid drainage system.

By improving sustained functionality and measurement accuracy, impairment of functionality and measurement accuracy is inhibited.

Thus, the present invention relates to a method for inhibiting impairment of functionality and accuracy in a body fluid measurement system having inner surfaces coming into contact with body fluid, the method comprising the following step(s):

applying an oil mixture to the inner surfaces of the body fluid drainage system.

The oil mixture is preferably applied to inner surfaces of the body fluid drainage system by self-priming with aid of the body fluid. The oil mixture may be applied to inner surfaces of the body fluid drainage system by self-priming with aid of the body fluid flowing through the system.

The method may comprise the step spreading the oil mixture on top of the body fluid. This step may be performed before the step applying an oil mixture to the inner surfaces of the body fluid drainage system.

In one embodiment, the oil mixture is applied to the inner surfaces of the body fluid drainage system when the level of body fluid in the body fluid drainage system increases. This may be combined with the step spreading the oil mixture on top of the body fluid. This is a way to achieve self-priming of the inner surfaces with the oil mixture aided by the body fluid.

In one embodiment, the body fluid takes with it the oil mixture when the level of body fluid in the drainage system increases during filling of the system and thereby the oil mixture is brought in contact with and adheres to the inner surfaces.

The body fluid may take with it the oil mixture when the level of body fluid in a chamber of the drainage system increases during filling of the chamber and thereby the oil mixture is brought in contact with and adheres to the inner surfaces.

The method may comprise the step adhering the oil mixture to the inner surfaces. This step may be performed in combination with and after the step spreading the oil mixture on top of the body fluid. This is a way to achieve self-priming of the inner surfaces with the oil mixture aided by the body fluid.

The oil mixture may be spread on top of the body fluid, brought into contact with the inner surfaces by the body fluid and adhere to the inner surfaces. Thereby, the oil mixture is applied to the inner surfaces of the body fluid drainage system by self-priming. The body fluid may take with it the oil mixture when the level of body fluid in the drainage system increases during filling of the system and thereby the oil mixture is brought in contact with and adheres to the inner surfaces.

The oil mixture may be applied to the inner surfaces of the body fluid drainage system by providing a water-soluble capsule in the body fluid handling system. The water-soluble capsule may be provided in the body fluid handling system upstream of a measurement portion and a siphoning portion of a body fluid chamber of the system.

When the oil mixture has been released the oil mixture is spread on top of the body fluid, since body fluid is an aqueous and oil repellent fluid. The oil mixture forms a layer on top of the body fluid. When the amount of body fluid in the body fluid drainage system and thus the level of body fluid in the body fluid drainage system increases the oil mixture that is floating on top of the body fluid is brought in contact with the inner surfaces of the body fluid drainage system. The oil mixture adheres to the inner surfaces and is applied to the inner surfaces. Thereby, the oil mixture is applied to the inner surfaces before the body fluid reaches higher levels of the inner surfaces. Thus, the oil mixture prevents or at least makes it more difficult for the body fluid to come into direct contact with the inner surfaces of the body fluid drainage system. The oil mixture is moved by the body fluid when the level of body fluid increases and thereby the oil mixture is applied to the inner surfaces of the body fluid drainage system just before the body fluid reaches a higher level in the body fluid drainage system. Thus, the inner surfaces are freshly coated with the oil mixture when the body fluid reaches the inner surfaces. After emptying of the body fluid drainage system, the oil mixture is applied again on the inner surfaces before the body fluid reaches the inner surfaces. Thus, the inner surfaces are always freshly coated with the oil mixture when body fluid reaches the inner surfaces. Thereby, an improved resistance against degeneration of the inner surfaces of the body fluid drainage system is achieved. Consequently, the functionality of the body fluid drainage system, such as the functionality of the siphoning self-emptying arrangement, is improved. For example is the degradation of the surfaces of the siphoning self-emptying arrangement inhibited and thus the siphoning effect is maintained. The functionality over time is improved and impairment of the functionality is inhibited. Also the measurement accuracy of the body fluid drainage system, such as the measurement accuracy of the capacitive measurement system, is improved. For example is the degradation of the surfaces of the wall of the measurement chamber through which the capacitive measurement system senses signals inhibited and thus the sensing ability is maintained. The measurement accuracy over time is improved and impairment of the measurement accuracy is inhibited.

The body fluid drainage system may comprise a body fluid measurement chamber. The body fluid drainage system may comprise electrodes arranged outside but close to the measurement chamber. The electrodes may be arranged to measure changing capacitance values as body fluid level inside the chamber increases. The electrodes may be arranged on the outside of the measurement chamber. The electrodes may be arranged on the outer surface of the measurement chamber. The electrodes may be integrated in the measurement chamber. The electrodes may be integrated in the measurement chamber on the outside of the measurement chamber.

In one embodiment, the present invention relates to a body fluid drainage system comprising a body fluid measurement chamber, wherein the body fluid measurement system comprises an electronic measurement system comprising electrodes arranged outside but close to said measurement chamber to measure changing capacitance values as body fluid level inside the chamber increases, wherein an oil mixture is arranged in the luminal space of the body fluid drainage system, wherein the oil mixture comprises 90-100% of an oil selected from the group consisting of silicone fluids and mineral oils or a mixture thereof, and having a viscosity of at most 600 cSt.

In one embodiment, the present invention relates to a body fluid drainage system comprising a body fluid chamber, wherein the body fluid chamber comprises a self-emptying siphoning arrangement arranged to empty itself by means of siphoning technique, wherein an oil mixture is arranged in the luminal space of the body fluid drainage system, wherein the oil mixture comprises 90-100% of an oil selected from the group consisting of silicone fluids and mineral oils or a mixture thereof, and having a viscosity of at most 600 cSt. The self-emptying siphoning arrangement may be arranged to empty itself by means of siphoning technique when a certain volume of body fluid is present in the body fluid chamber.

In one embodiment, the present invention relates to a body fluid drainage system comprising a body fluid measurement chamber and an electronic measurement system comprising electrodes arranged outside but close to said measurement chamber to measure changing capacitance values as body fluid level inside the chamber increases, wherein the capsule of the present invention is arranged in the luminal space of the measurement system.

In one embodiment, the present invention relates to a body fluid drainage system comprising a body fluid chamber, wherein the body fluid chamber comprises a self-emptying siphoning arrangement arranged to empty itself by means of siphoning technique, wherein the capsule of the present invention is arranged in the luminal space of the system. The self-emptying siphoning arrangement may be arranged to empty itself by means of siphoning technique when a certain volume of body fluid is present in the body fluid chamber.

In one embodiment the present invention relates to a body fluid drainage system comprising a body fluid measurement chamber, wherein the body fluid measurement system comprises an electronic measurement system comprising electrodes arranged outside but close to said measurement chamber to measure changing capacitance values as body fluid level inside the chamber increases and the body fluid measurement chamber comprises a self-emptying siphoning arrangement arranged to empty itself by means of siphoning technique, wherein the capsule of the present invention is arranged in the luminal space of the drainage system.

The present invention relates in an aspect to sterilisation, where the container, such as a capsule, is sterile and is sterilised by radiation sterilisation. Thereby, the surface protective fluid, such as the oil mixture, contained in the container is sterile. The present invention relates in an aspect to sterilisation, where the chamber of the body fluid drainage system is sterile and is sterilised by gas sterilisation. Thereby, the inner luminal surface of the chamber is sterile. In case the container, e.g. in the form a capsule, is present in the chamber also the surface of the container is sterile by the gas sterilisation. This is advantageous if the surface of the container has been contaminated during handling of the container, such as during insertion of a capsule into the chamber of the body fluid drainage system.

In particular, the present invention relates to a method for sterilising a body fluid drainage system for handling a body fluid ex vivo. The body fluid drainage system comprises a chamber. The method comprises the following steps:
providing a container containing a surface protective fluid to be released into the chamber of the body fluid drainage system,
subjecting the container to radiation sterilisation,
inserting the container into the chamber of the body fluid drainage system,
subjecting the chamber containing the container to gas sterilisation.

The present invention relates in particular also to a method for sterilising a body fluid drainage system for handling a body fluid ex vivo. The body fluid drainage system comprises a chamber. The method comprises the steps:
providing a container containing a surface protective fluid to be released into the chamber of the body fluid drainage system, which container has been subjected to radiation sterilisation,
inserting the container into the chamber of the body fluid drainage system, and
subjecting the chamber containing the container to gas sterilisation.

In this latter sterilising method, the container including the surface protective fluid has been subjected to radiation sterilisation, before inserting the container into the chamber of the body fluid drainage system. The container containing the surface protective fluid has been pretreated by radiation sterilisation, before inserting the container into the chamber of the body fluid drainage system.

The container is sterilised using radiation sterilisation so that both the surface and the content of the container is sterilised. The radiation sterilisation is performed according to applicable standards for medical devices. Ionizing radiation such as Beta, gamma or X-rays is used because of their ability to penetrate substances due to their short wavelength. The high intensity radiation destroys e.g. microorganisms. In a preferred embodiment gamma or Beta radiation is used for radiation sterilisation. In an even more preferred embodiment gamma radiation is used for radiation sterilisation. In an alternative embodiment Beta radiation is preferred.

The container and the chamber cannot be sterilised at the same time using the radiation sterilisation because the radiation can affect the material properties of the chamber. Radiation sterilisation may negatively affect the appearance and the surface properties of the chamber. For example, the surface properties may be changed so that biofilm forms easier on the surface. In the worst case the material of the chamber may be so affected so that the chamber is weakened and cannot hold body fluid. Therefore the container and the chamber is sterilised using gas sterilisation. The gas sterilisation is performed according to applicable standards for medical devices.

When inserting the container into the chamber of the body fluid drainage system the surface of the sterilised container may be contaminated during handling. Therefore the chamber is sterilised using gas sterilisation when the container is present in the chamber. That way both the inside surface of the chamber and the outside surface of the container are sterilised. Gas sterilisation is a surface steriliser and does not affect the content of the container. Gas sterilisation function by exposing the articles to be sterilized to high concentrations of reactive gases (for example alkylating agents such as ethylene oxide, and oxidizing agents such as hydrogen peroxide and ozone). In a preferred embodiment the gas sterilisation is an Ethylene Oxide (EtO) sterilisation.

The sterilisation provides a sterile product that can be stored for a prolonged time and which gives a high surface resistance against encrustation and bio film formation. Thereby, the accuracy and operational life time of the body fluid drainage system is increased.

In some aspects of the first method for sterilising, the method further comprises the step enclosing the container in a sealed enclosure, which enclosing step is performed before the step subjecting the container to radiation sterilisation. Thus, the container is enclosed in a sealed enclosure and thereafter subjected to radiation sterilisation. Both the container and the sealed enclosure are subjected to radiation sterilisation.

In some aspects of the second method for sterilising, the provided container has been enclosed in a sealed enclosure before it was subjected to radiation sterilisation. Thus, the container has been enclosed in a sealed enclosure and thereafter subjected to radiation sterilisation. Both the container and the sealed enclosure have been subjected to radiation sterilisation.

The sealed enclosure inhibits contamination of the surface of the container, e.g. during handling before insertion into the chamber of the body fluid drainage system such as during storage or during transport between the equipment for radiation sterilisation and the equipment for gas sterilisation. The sealed enclosure may be a plastic bag that preferably is sealed by welding. Alternatively, the sealed enclosure may be a box or any other suitable sealed or sealable receptacle.

In some aspects, the sealed enclosure comprises two layers of sealed enclosures. The container may be placed in a first (inner) sealed enclosure and the first (inner) sealed enclosure may be placed in a second (outer) sealed enclosure. Both the first and the second sealed enclosures may be a plastic bag that preferably is sealed by welding, i.e. the sealed enclosure may comprise two plastic bags that preferably are sealed by welding. The enclosing of the container in a sealed enclosure is preferably performed in a cleanroom. The container including the first and second enclosures that have been subjected to radiation sterilisation can be brought into the airlock of a cleanroom. In the airlock, the second (outer) enclosure can be removed and then the first (inner) enclosure is clean such that it can be brought into the cleanroom. The first (inner) enclosure can be removed and the container can be inserted into the chamber of the body fluid drainage system in a cleanroom. The insertion of the container into the chamber of the body fluid drainage system is preferably performed in a cleanroom.

In some aspects of the method for sterilising, the container is a capsule comprising a capsule wall made of a water-soluble material.

In some aspects of the method for sterilising, the surface protective fluid is an oil mixture comprising 90-100% of an oil selected from the group consisting of silicone fluids and mineral oils or a mixture thereof, and having a viscosity of at most 600 cSt.

Further, the present invention relates in particular to a body fluid drainage system for handling a body fluid ex vivo, wherein the body fluid drainage system comprises a chamber, wherein the body fluid drainage system further comprises a container containing a surface protective fluid, wherein the container is arranged to release the surface protective fluid into the chamber, wherein the surface protective fluid is sterilised by radiation sterilisation and wherein an outer surface of the container and at least the chamber of the body fluid drainage system is sterilised by gas sterilisation.

The present invention relates in particular also to a body fluid drainage system for handling a body fluid ex vivo, wherein the body fluid drainage system comprises a chamber, wherein the body fluid drainage system further comprises a container containing a surface protective fluid, wherein the container is arranged to release the surface protective fluid into the chamber, wherein the body fluid drainage system is sterilised by any of the above methods for sterilisation.

In some aspects of the body fluid drainage system, the container is disposed in the chamber In some aspects of the body fluid drainage system, the container is a capsule comprising a capsule wall made of a water-soluble material.

In some aspects of the body fluid drainage system, the surface protective fluid is an oil mixture comprising 90-100% of an oil selected from the group consisting of silicone fluids and mineral oils or a mixture thereof, and having a viscosity of at most 600 cSt.

The body fluid may be urine.

Capsule

The oil releasing device, e.g. the container, is preferably implemented as a capsule 105 comprising a capsule wall made of a water-soluble material. The capsule encapsulates an amount of oil. The capsule is preferably of a shape selected from the group of cylindrical, cylindrical with hemispherical ends, spherical, oval, elliptical or of a shape rounded cubic or tablet, or of any shape suitable to the purpose.

The material of the capsule wall is a water-soluble material, preferably one that disintegrates in a few minutes when exposed to body fluid flow. One preferred material of the capsule wall is polyvinyl alcohol (PVOH). Most preferred, however, the material of the capsule wall is hydroxypropyl methylcellulose, such as for example the material of LICAPS capsules from CAPSUGEL-www.capsugel.com. One particular advantage of PVOH is a very quick release of the oil because of fast disintegration. One advantage of hydroxypropyl methylcellulose is its stability which facilitates handling, storage and transportation.

In one embodiment, the material of the capsule wall disintegrates within one hour. Thereby, the material of the capsule wall is disintegrated within one hour after is has been exposed to body fluid. This has the advantage that the oil mixture in the capsule is rapidly released and the thus the protection of the inner surfaces of the body fluid handling system is rapidly established. The material of the capsule wall may disintegrate within 30 minutes after exposure to body fluid, such as within 15 minutes, such as within 10 minutes, such as within about 5 minutes. The material of the capsule wall may disintegrate within a few minutes. The material of the capsule wall may disintegrate within a few minutes after exposure to body fluid. The material of the capsule wall is preferably totally disintegrated within the above specified time intervals.

In addition to improved accuracy, such as measurement accuracy, and operational life of the chamber, the capsule allows that the oil, as an active ingredient, is inactive during shelf life and activated first in the clinical setting.

The capsule provides a convenient way of storing and handling the oil mixture during transport and storage of a body fluid drainage system. The capsule also provides a convenient way of activating the protection of the inner surfaces of the body fluid drainage system in the clinical situation, i.e. when the body fluid drainage system is to be put in operation. The capsule can be stored in the body fluid drainage system or separately up until use of the body fluid drainage system. Since the oil mixture not is applied to the inner surfaces of the body fluid drainage system before use of the body fluid drainage system, the protection of the oil mixture provided to the inner surfaces is not damaged or deteriorated before use of the body fluid measurement system. If not stored in the body fluid drainage system, the capsule is inserted in the body fluid drainage system before use. When the body fluid drainage system is to put into use, the body fluid that is entering the body fluid drainage system dissolves the water-soluble material of the capsule wall releasing the oil mixture. The oil mixture is transported with the body fluid into the chamber and the oil mixture is thereby distributed into the chamber. The water-soluble material is preferably disintegrated in a few minutes when exposed to body fluid in order to release the oil mixture rapidly and to rapidly establish the application of the oil mixture on the inner surfaces of the body fluid drainage system aided by the body fluid as described above. Thereby, the protection of the inner surfaces of the body fluid drainage system is rapidly established.

To prevent the capsule from interfering with body fluid flow in the chamber it is advantageous to provide a grate 110 or similar arrangement to prevent early, non dissolved fragments of the capsule to clog the flow of body fluid. It is also advantages to provide such a grate to confine the capsule during transport and pre-use to an upper portion of the chamber.

Thus, the grate 110 is arranged to prevent pieces of non-dissolved capsule from travelling with the body fluid flow and temporarily blocking possible valves or siphoning system. The term "chamber" may be used as a general term denoting the whole chamber comprising a first portion 115, i.e., an inlet upstream portion or "atrium", a second portion 120 midstream which is the actual measurement portion of the chamber presenting important surfaces for the sensors. Further downstream is provided a third portion 130, 140 providing the self-emptying siphoning arrangement 130 and outlet piping 140. To be able to treat the surfaces of the second portion 120 and the third portion 130 with oil from the capsule, the capsule is provided in the first portion 115, the atrium. The grate 110 is arranged between the atrium 115 and the second portion 120 of the chamber 101.

Oil

The oil is a purpose selected oil. Viscosity may be at most 600 centiStoke (cSt, $mm^2/s$). Viscosity is preferably in the interval of 200 to 600 centiStoke (cSt, $mm^2/s$). Viscosity is more preferred in the interval of 300 to 400 centiStoke (cSt, $mm^2/s$). Viscosity is even more preferred in the interval of 345 to 355 centiStoke (cSt, $mm^2/s$). An oil having a viscosity of at most 600 cSt or within these intervals is spread on top of body fluid and forms a layer of the oil on top of the body fluid. The oil is spread over the surface of the body fluid. An oil having such viscosities is spread on top of the body fluid, is brought in contact with the inner surfaces of the body fluid drainage system and is applied to the inner surfaces of the body fluid drainage system in the way described above. A too high viscosity will result in that oil not is spread over the surface of body fluid and thereby not is brought in contact with inner surfaces of a body fluid drainage system and nor is applied to inner surfaces of a body fluid drainage system. Instead an oil having a too high viscosity will accumulate and form a clump.

The oil is preferably of a grade approved for medical use. It is preferably an oil comprising as a major constituent an oil preferably selected from the group of silicone fluids or mineral oils or from a combination thereof.

The silicon oil is preferably selected from polydimethylsiloxanes, polymethylphenylsiloxanes, polydipropylsiloxanes, and polyphenylsiloxanes. More preferably the silicon oil is selected from polydimethylsiloxanes. More preferred is an oil composition selected from the group of linear polydimethylsiloxanes, such as for example SILBIONE oil 70047 V 350 from Bluestar Silicones—www.blustarsilicones.com. Most preferred is an oil comprising 90-100% silicone oil of viscosity about 350 cSt. The oil may be free of additive, or may comprise one or more additives.

The volume of oil provided in the capsule to achieve the described has been tested and effect is achieved with a volume of 0.5 ml of oil.

The capacitive sensors are not influenced, or being influenced only negligible by the oil mixture.

Oil Treatment

The inventors have also generalised that the purpose selected oil disclosed above may be applied to body fluid handling system surfaces using other methods than by capsule.

Thus a specific use of the oil is made an object of the present invention; It is disclosed the use of a compound X in the application Y, wherein the compound X is an oil mixture comprising 90-100% of an oil selected from the group consisting of silicone fluids and mineral oils or a mixture thereof, and having a viscosity of at most 600 cSt, preferably within the interval of 300 to 400 cSt, more preferred within the interval of 300 to 400 cSt, even more preferred 345 to 355 cSt, and most preferred about 350 cSt, and wherein the application Y is the treatment of luminal surfaces of a body fluid handling system or a body fluid drainage system. With the term "treatment" is here meant an activity wherein the oil is applied to the surface in question regardless of the method of distribution of the oil into the luminal space of the body fluid handling system. Preferred methods include pouring oil into the luminal space, spraying, painting, immersion, soaking, releasing, and distribution with the aid of a aqueous fluid. The aqueous fluid may be body fluid. In particular is distribution involving release of the oil mixture from a capsule as described above preferred and more preferred is distribution from such a capsule where the released oil mixture is transported into the luminal space with the body fluid. In one particular embodiment is the container a syringe and the surface protective fluid is contained in the syringe. The surface protective fluid is then manually released form the syringe to the chamber e.g. by pressing the plunger of the syringe. The surface protective fluid is preferably distributed into the chamber in connection with the start of the operation of the drainage system. The surface protective fluid is then preferably transported into the luminal space and spread over the surfaces of the luminal space with the body fluid as described above.

Regardless of the method of distribution of the oil mixture into the luminal space, the oil mixture may be applied to the luminal surfaces of the body fluid handling system by self-priming as described above.

In the present invention the oil treatment as described is taught as single step of treatment of the surfaces for increased operational time. The oil is a non-complex compound involving no other substance, like an antimicrobial agent, such as for example chlorhexidine. It is an advantage that no other substance, like an antimicrobial agent, such as for example chlorhexidine, is needed. The oil mixture may advantageously be void of such antimicrobial substance. This is also true regarding the oil mixture when released by capsule.

Material of Chamber

The material of the chamber is preferably a polymer of medical equipment grade. More preferred the material of the chamber is a polymer of medical equipment grade, wherein the polymer exhibits a lipophilic surface. Most preferred the material of the chamber is polypropylene. Tests have shown that lipophilic material keep the oil at the chamber surface, in contrast to a lipophobic material which will repel the oil. Thus, with a lipophobic material the oil would be washed away by the body fluid rather quickly by time.

EXAMPLES/TESTS

The following table illustrates a combination of capsule material, oil, and chamber material.

| EXAMPLE | Capsule material | Oil/viscosity | Chamber material | Prolonged operational time (%) |
|---|---|---|---|---|
| EX A | hydroxypropyl methylcellulose | Silicone/ 350 cSt | poly- propylene | 480 to 840 |

A series of tests with a body fluid measurement system, wherein the body fluid is urine, having an electronic measurement system and a self-emptying siphoning arrangement have been performed. The time until surface degradation in the form of biofilm formation were determined by measuring the time until either the electronic measurement signal is unsatisfactory or disappears or until the function of the self-emptying siphoning arrangement is unsatisfactory or ceases. The material of the measurement chamber of the measurement system is polypropylene. Tests were performed with and without oil. In tests involving an oil, the oil was supplied by means of a capsule. The oil as well as the material of the capsule wall is specified in the table above. Two different samples of urine were tested and the results are presented below.

| | | Time until surface degradation in hours | |
|---|---|---|---|
| Test number | Urine sample | With oil | Without oil |
| 1 | 1 | 479 | |
| 2 | 1 | | 68 |
| 3 | 1 | | 68 |
| 4 | 1 | | 57 |
| 5 | 1 | | 74 |
| 6 | 2 | 336 | |
| 7 | 2 | | 70 |
| 8 | 2 | | 58 |

For urine sample 1 the operational time until surface degradation increased from 57-74 hours without oil to 479 hours when having an oil present, which corresponds to an prolonged operational time of 650-840%. For urine sample 2 the operational time until surface degradation increased from 58-70 hours without oil to 336 hours when having an oil present, which corresponds to an prolonged operational time of 480-580%.

According to some aspects there is provided a body fluid drainage system container for releasing a surface protective fluid into a lumen of a body fluid drainage system handling a body fluid ex vivo. The container contains a surface protective fluid and the container is adapted to release the surface protective fluid when the body fluid drainage system is put in operation.

The body fluid drainage system container wherein, according to some aspects, the surface protective fluid is sterile.

The body fluid drainage system container wherein, according to some aspects, the surface protective fluid is sterilised by radiation sterilisation.

The body fluid drainage system container wherein, according to some aspects, the container is a capsule comprising a capsule wall made of a water-soluble material.

The body fluid drainage system container wherein, according to some aspects, the surface protective fluid is an oil mixture comprising 90-100% of an oil selected from the group consisting of silicone fluids and mineral oils or a mixture thereof, and having a viscosity of at most 600 cSt.

According to some aspects there is provided a body fluid drainage system for handling a body fluid ex vivo. The body fluid drainage system comprises a chamber and the body fluid drainage system further comprises a container containing a surface protective fluid, wherein the container is arranged to release the surface protective fluid into the chamber.

The body fluid drainage system wherein, according to some aspects, the container is disposed in the chamber.

The body fluid drainage system wherein, according to some aspects, the container is a container as previously described.

The body fluid drainage system wherein, according to some aspects, at least the chamber of the body fluid drainage system is sterile.

The body fluid drainage system wherein, according to some aspects, at least the chamber of the body fluid drainage system is sterilised by gas sterilisation.

The body fluid drainage system wherein, according to some aspects, the surface protective fluid is sterilised by radiation sterilisation and wherein an outer surface of the container and at least the chamber of the body fluid drainage system is sterilised by gas sterilisation.

The body fluid drainage system wherein, according to some aspects, the container is a capsule comprising a capsule wall made of a water-soluble material.

The body fluid drainage system wherein, according to some aspects, the surface protective fluid is an oil mixture comprising 90-100% of an oil selected from the group consisting of silicone fluids and mineral oils or a mixture thereof, and having a viscosity of at most 600 cSt.

According to some aspects there is provided a method for sterilising a body fluid drainage system for handling a body fluid ex vivo. The body fluid drainage system comprises a chamber. The method comprises the following steps:

providing a container containing a surface protective fluid to be released into the chamber of the body fluid drainage system, subjecting the container to radiation sterilisation, inserting the container into the chamber of the body fluid drainage system, subjecting the chamber containing the container to gas sterilisation.

According to some aspects there is provided a method for sterilising a body fluid drainage system for handling a body fluid ex vivo. The body fluid drainage system comprises a chamber. The method comprises the steps:

providing a container containing a surface protective fluid to be released into the chamber of the body fluid drainage system, which container has been subjected to radiation sterilisation, inserting the container into the chamber of the body fluid drainage system, and subjecting the chamber containing the container to gas sterilisation.

The first method for sterilising wherein, according to some aspects, the method further comprises the step enclosing the container in a sealed enclosure, which enclosing step is performed before the step subjecting the container to radiation sterilisation.

The second method for sterilising wherein, according to some aspects, the provided container has been enclosed in a sealed enclosure before it was subjected to radiation sterilisation.

The method for sterilising wherein, according to some aspects, the container is a container as previously described.

The method for sterilising wherein, according to some aspects, the body fluid drainage system is a body fluid drainage system as previously described.

The method for sterilising wherein, according to some aspects, the container is a capsule comprising a capsule wall made of a water-soluble material.

The method for sterilising wherein, according to some aspects, the surface protective fluid is an oil mixture comprising 90-100% of an oil selected from the group consisting of silicone fluids and mineral oils or a mixture thereof, and having a viscosity of at most 600 cSt.

According to some aspects there is provided a body fluid drainage system for handling a body fluid ex vivo, wherein the body fluid drainage system comprises a chamber, wherein the body fluid drainage system further comprises a container containing a surface protective fluid, wherein the container is arranged to release the surface protective fluid into the chamber, wherein the body fluid drainage system is sterilised by any of the above methods for sterilisation.

The body fluid drainage system wherein, according to some aspects, the container is disposed in the chamber.

The body fluid drainage system wherein, according to some aspects, the container is a container as previously described.

The body fluid drainage system wherein, according to some aspects, the container is a capsule comprising a capsule wall made of a water-soluble material.

The body fluid drainage system wherein, according to some aspects, the surface protective fluid is an oil mixture comprising 90-100% of an oil selected from the group consisting of silicone fluids and mineral oils or a mixture thereof, and having a viscosity of at most 600 cSt.

According to some aspects there is provided a capsule for releasing an oil mixture in a lumen of a system handling a body fluid. The capsule comprising a capsule wall defining a space filled with an oil mixture. The oil mixture comprises 90-100% of an oil selected from the group consisting of silicone fluids and mineral oils or a mixture thereof, and having a viscosity of at most 600 cSt, and wherein the capsule wall is made of a water-soluble material.

The capsule wherein, according to some aspects, the water-soluble material is selected from the group consisting of hydroxypropyl methylcellulose and polyvinyl alcohol (PVOH) or a mixture thereof.

The capsule wherein, according to some aspects, the oil mixture is selected from the group of silicone fluids.

The capsule wherein, according to some aspects, the oil mixture is selected from the group of linear polydimethylsiloxanes.

The capsule wherein, according to some aspects, the viscosity of the oil is in the interval of 200 to 600 cSt, such as in the interval of 300 to 400 cSt, such as in the interval of 345 to 355 cSt, such as about 350.

The capsule wherein, according to some aspects, the oil mixture is sterile.

The capsule wherein, according to some aspects, the oil mixture is sterilised by radiation sterilisation.

According to some aspects there is provided a body fluid drainage system comprising a chamber, wherein an oil mixture is arranged in the chamber of the body fluid drainage system. The oil mixture comprises 90-100% of an oil selected from the group consisting of silicone fluids and mineral oils or a mixture thereof, and having a viscosity of at most 600 cSt.

The body fluid drainage system further comprises, according to some aspects, an electronic measurement system comprising electrodes arranged outside said chamber to measure changing capacitance values as body fluid level inside the chamber increases.

The body fluid drainage system wherein, according to some aspects, the chamber comprises a self-emptying siphoning arrangement arranged to empty itself by means of siphoning technique.

The body fluid drainage system wherein, according to some aspects, the viscosity of the oil is in the interval of 200 to 600 cSt, such as in the interval of 300 to 400 cSt, such as in the interval of 345 to 355 cSt, such as about 350.

The body fluid drainage system wherein, according to some aspects, a capsule as previously described is arranged in the luminal space of the body fluid drainage system.

The body fluid drainage system wherein, according to some aspects, the capsule is arranged upstream of the chamber or in an upstream portion of the chamber and is prevented from entering the chamber by a grate.

The body fluid drainage system wherein, according to some aspects, the grate is made of a metal or polymer material.

The body fluid drainage system wherein, according to some aspects, the material of the chamber is selected from a group consisting of polymer materials.

The body fluid drainage system wherein, according to some aspects, the material of the chamber is selected from a group consisting of glass materials.

The body fluid drainage system wherein, according to some aspects, the material of the chamber is selected from a group of materials having lipophilic properties The body fluid drainage system wherein, according to some aspects, at least the chamber of the body fluid drainage system is sterile.

The body fluid drainage system wherein, according to some aspects, at least the chamber of the body fluid drainage system is sterilised by gas sterilisation.

According to some aspects there is provided a method for inhibiting impairment of functionality in a body fluid drainage system having inner surfaces coming into contact with body fluid. The method comprising the following step(s):
  applying an oil mixture to the inner surfaces of the body fluid drainage system by self-priming with the aid of the body fluid.

The method comprises, according to some aspects, the step spreading the oil mixture on top of the body fluid.

The method wherein, according to some aspects, the oil mixture is applied to the inner surfaces of the body fluid drainage system when the level of body fluid in the body fluid drainage system increases.

The method wherein, according to some aspects, the body fluid takes with it the oil mixture when the level of body fluid in the body fluid drainage system increases during filling of the system and thereby the oil mixture is brought in contact with and adheres to the inner surfaces.

The method wherein, according to some aspects, the oil mixture comprises 90-100% of an oil selected from a group consisting of silicone fluids, and mineral oils, or from a mixture thereof.

The method wherein, according to some aspects, the oil has a viscosity of at most 600 cSt, such as in the interval of 200 to 600 cSt, such as in the interval of 300 to 400 cSt, such as in the interval of 345 to 355 cSt, such as of about 350 cSt.

The method wherein, according to some aspects, the oil mixture is applied by connecting a patient's drainage with the body fluid drainage system as previously described provided with the capsule as previously described.

According to some aspects there is provided a use of an oil mixture in treatment of luminal surfaces of a body fluid drainage system. The oil mixture comprises 90-100% of an oil selected from the group consisting of silicone fluids and mineral oils or a mixture thereof, and having a viscosity of at most 600 cSt.

The use wherein, according to some aspects, the viscosity is in the interval of 200 to 600 cSt, such as 300 to 400 cSt, such as 345 to 355 cSt, such as about 350.

The use wherein, according to some aspects, the oil mixture is void of antimicrobial agent.

The invention claimed is:

1. A method for sterilising a body fluid drainage system for handling a body fluid ex vivo, wherein the body fluid drainage system comprises a chamber, wherein the method comprises the steps
   providing a container containing a surface protective fluid to be released into the chamber of the body fluid drainage system, wherein the surface protective fluid adheres to inner surface of the chamber and prevents other fluids from coming into contact with the surface,
   subjecting the container to radiation sterilisation,
   inserting the container into the chamber of the body fluid drainage system, and
   subjecting the chamber containing the container to gas sterilisation.

2. The method according to claim 1, wherein the method further comprises the step enclosing the container in a sealed enclosure, which enclosing step is performed before subjecting the container to radiation sterilisation.

3. The method for sterilising a body fluid drainage system for handling a body fluid ex vivo, wherein the body fluid drainage system comprises a chamber, wherein the method comprises the steps
   providing a container containing a surface protective fluid to be released into the chamber of the body fluid drainage system, which container has been subjected to radiation sterilisation, wherein the surface protective fluid adheres to inner surface of the chamber and prevents other fluids from coming into contact with the surface,
   inserting the container into the chamber of the body fluid drainage system, and
   subjecting the chamber containing the container to gas sterilisation.

4. The method according to claim 3, wherein the provided container has been enclosed in a sealed enclosure before it was subjected to radiation sterilisation.

5. The method according to claim 1, wherein the container is a capsule comprising a capsule wall made of a water-soluble material.

6. The method according to claim 1, wherein the surface protective fluid is an oil mixture comprising 90-100% of an oil selected from the group consisting of silicone fluids and mineral oils or a mixture thereof, and having a viscosity of at most 600 cSt.

7. The method according to claim 2, wherein the container is a capsule comprising a capsule wall made of a water-soluble material.

8. The method according to claim 3, wherein the container is a capsule comprising a capsule wall made of a water-soluble material.

9. The method according to claim 4, wherein the container is a capsule comprising a capsule wall made of a water-soluble material.

10. The method according to claim 2, wherein the surface protective fluid is an oil mixture comprising 90-100% of an oil selected from the group consisting of silicone fluids and mineral oils or a mixture thereof, and having a viscosity of at most 600 cSt.

11. The method according to claim 3, wherein the surface protective fluid is an oil mixture comprising 90-100% of an oil selected from the group consisting of silicone fluids and mineral oils or a mixture thereof, and having a viscosity of at most 600 cSt.

12. The method according to claim 4, wherein the surface protective fluid is an oil mixture comprising 90-100% of an oil selected from the group consisting of silicone fluids and mineral oils or a mixture thereof, and having a viscosity of at most 600 cSt.

13. The method according to claim 5, wherein the surface protective fluid is an oil mixture comprising 90-100% of an oil selected from the group consisting of silicone fluids and mineral oils or a mixture thereof, and having a viscosity of at most 600 cSt.

* * * * *